US011286414B2

(12) United States Patent
Fida et al.

(10) Patent No.: US 11,286,414 B2
(45) Date of Patent: Mar. 29, 2022

(54) SODIUM NITROPRUSSIDE AND NITRATE METABOLIC INHIBITION OF SULFATE-REDUCING MICROBES TO CONTROL SULFIDE PRODUCTION

(71) Applicant: UTI Limited Partnership, Calgary (CA)

(72) Inventors: Tekle Fida, Calgary (CA); Gerrit Voordouw, Calgary (CA); Jaspreet Mand, Calgary (CA)

(73) Assignee: UTI Limited Partnership, Calgary (CA)

( * ) Notice: Subject to any disclaimer, the term of this patent is extended or adjusted under 35 U.S.C. 154(b) by 1 day.

(21) Appl. No.: 16/645,531

(22) PCT Filed: Sep. 7, 2018

(86) PCT No.: PCT/CA2018/051097
§ 371 (c)(1),
(2) Date: Mar. 9, 2020

(87) PCT Pub. No.: WO2019/046958
PCT Pub. Date: Mar. 14, 2019

(65) Prior Publication Data
US 2020/0277525 A1   Sep. 3, 2020

Related U.S. Application Data

(60) Provisional application No. 62/556,038, filed on Sep. 8, 2017.

(51) Int. Cl.
*C09K 8/524* (2006.01)
*C09K 8/54* (2006.01)
(Continued)

(52) U.S. Cl.
CPC ............... *C09K 8/524* (2013.01); *C09K 8/54* (2013.01); *C10G 75/02* (2013.01); *C12N 1/38* (2013.01); *C09K 2208/20* (2013.01)

(58) Field of Classification Search
None
See application file for complete search history.

(56) References Cited

U.S. PATENT DOCUMENTS

| | | | | |
|---|---|---|---|---|
| 2009/0214674 A1* | 8/2009 | Barraud | ................. | A01N 59/00 424/718 |
| 2014/0295523 A1* | 10/2014 | Steer | ....................... | C09K 8/90 435/209 |
| 2018/0251808 A1* | 9/2018 | Van Der Kraan | ....... | C12Q 1/64 |

FOREIGN PATENT DOCUMENTS

WO   2006/125262 A1   11/2006

OTHER PUBLICATIONS

Barraud N, Hassett DJ, Hwang S-H, Rice SA, Kjelleberg S, Webb JS. (2006). Involvement of nitric oxide in biofilm dispersal of Pseudomonas aeruginosa. Journal of Bacteriology 188: 7344-7353.
(Continued)

*Primary Examiner* — John J Figueroa
(74) *Attorney, Agent, or Firm* — FisherBroyles LLP; Anthony J DoVale (57) ABSTRACT

Combinations of a nitroprusside, such as sodium nitroprusside (SNP; $Na_2[Fe(CN)_5NO].2H_2O$) and a nitrate, are provided, together with methods for the combined use of the nitroprusside and the nitrate as metabolic inhibitors of microbial cultures. The microbial cultures may include sulfate reducing bacteria (SRB) in aqueous culture. This metabolic inhibition may for example be implemented in the presence of a hydrocarbon, for example in an oil reservoir or in oil field systems and facilities. When applied to an SRB culture in the presence of a hydrocarbon, the combination of
(Continued)

the nitroprusside and the nitrate may accordingly be used to ameliorate the biological formation of sulfides, particularly hydrogen sulfide.

20 Claims, 11 Drawing Sheets

(51) Int. Cl.
    *C10G 75/02*     (2006.01)
    *C12N 1/38*     (2006.01)

(56) References Cited

OTHER PUBLICATIONS

Bødtker G, Thorstenson T, Lillebo BL, Thorbjornsen BE, Ulvoen RH, Sunde E, Torsvik T (2008). The effect of long-term nitrate treatment on SRB activity, corrosion rate and bacterial community composition in offshore water injection systems. J Ind Microbiol Biotechnol 35: 1625-1636.

Callbeck CM, Agrawal A, Voordouw G. (2013). Acetate production from oil under sulfate-reducing conditions in bioreactors injected with sulfate and nitrate. Appl Environ Microbiol 79: 5059-5068.

Correa LA, Baptista W, Ferreira LA. (2002). Wet H2S and CN— corrosion control through on-site polysulfide generation, 6th conf. on Equipment Technology (Salvador Bahia, Brazil: The Brazilian Association of Non-Destructive Testing and Inspection).

Cortese-Krott MM, Fernandez BO, Santos JL, Mergia E, Grman M, Nagy P et al. (2014). Nitrosopersulfide (SSNO-) accounts for sustained NO bioactivity of S-nitrosothiols following reaction with sulfide. Redox Biol 2: 234-244.

Fida TT, Palamuru S, Pandey G, Spain JC. (2014). Aerobic biodegradation of 2,4-dinitroanisole by *Nocardioides* sp. strain JS1661. Appl Environ Microbiol 80: 7725-7731.

Filipovic MR, Eberhardt M, Prokopovic V, Mijuskovic A, Orescanin-Dusic Z, Reeh P et al. (2013). Beyond H2S and NO Interplay: Hydrogen Sulfide and Nitroprusside React Directly to Give Nitroxyl (HNO). A New Pharmacological Source of HNO. Journal of Medicinal Chemistry 56: 1499-1508.

Fraise AP. (2002). Biocide abuse and antimicrobial resistance—a cause for concern? J Antimicrob Chemother 49: 11-12.

Gassara F, Suri N, Stanislav P, Voordouw G. (2015). Microbially enhanced oil recovery by sequential injection of light hydrocarbon and nitrate in low- and high-pressure bioreactors. Environ Sci Technol 49: 12594-12601.

Gieg LM, Jack TR, Foght JM. (2011). Biological souring and mitigation in oil reservoirs. Appl Microbiol Biotechnol 92: 263-282.

Grigoryan AA, Cornish SL, Buziak B, Lin S, Cavallaro A, Arensdorf JJ et al. (2008). Competitive oxidation of volatile fatty acids by sulfate- and nitrate-reducing bacteria from an oil field in Argentina. Appl Environ Microbiol 74: 4324-4335.

Hubert C, Nemati M, Jenneman G, Voordouw G. (2003). Containment of biogenic sulfide production in continuous up-flow packed-bed bioreactors with nitrate or nitrite. Biotechnol Prog 19: 338-345.

Hubert C, Nemati M, Jenneman G, Voordouw G. (2005). Corrosion risk associated with microbial souring control using nitrate or nitrite. Appl Microbiol Biotechnol 68: 272-282.

Joannou CL, Cui X-Y, Rogers N, Vielotte N, Torres Martinez CL, Vugman NV et al. (1998). Characterization of the bactericidal effects of sodium nitroprusside and other pentacyanonitrosyl complexes on the food spoilage bacterium Clostridium sporogenes. Applied and Environmental Microbiology 64: 3195-3201.

Kjellerup BV, Veeh RH, Sumithraratne P, Thomsen TR, Buckingham-Meyer K, Frolund B et al. (2005). Monitoring of microbial souring in chemically treated, produced-water biofilm systems using molecular techniques. J Ind Microbiol Biotechnol 32: 163-170.

Koslyk JL, Ducci RD, Novak EM, Zetola VF, Lange MC. (2015). Sodium nitroprusside: low price and safe drug to control BP during thrombolysis in AIS. Arq Neuropsiquiatr 73: 755-758.

Lim HS, Zaphiriou A. (2016). Sodium nitroprusside in patients with mixed pulmonary hypertension and left heart disease: Hemodynamic predictors of response and prognostic implications. Journal of Cardiac Failure 22: 117-124.

Moore CM, Nakano MM, Wang T, Ye RW, Heimann JD. (2004). Response of Bacillus subtilis to nitric oxide and the nitrosating agent sodium nitroprusside. J Bacteriol 186: 4655-4664.

Quiroga SL, Almaraz AE, Amorebieta VT, Perissinotti LL, Olabe JA. (2011). Addition and redox reactivity of hydrogen sulfides (H2S/HS(-)) with nitroprusside: new chemistry of nitrososulfide ligands. Chemistry 17: 4145-4156.

Rock PA, Swinehart JH. (1966). The kinetics of the aqueous hydrogen sulfide-nitroprusside system. Inorganic Chemistry 5: 1078-1079.

Shen Y, Voordouw G (2015). Primers for dsr genes and Most Probable Number method for detection of sulfate-reducing bacteria in oil reservoirs. In, Hydrocarbon and Lipid Microbiology Protocols, McGenity, T., Timmis, K. and B. Nogales (eds), Springer-Verlag, Berlin Heidelberg. DOI 10.1007/8623_2015_72. pp. 1-9.

Tang K, Baskaran V, Nemati M. (2009). Bacteria of the sulphur cycle: An overview of microbiology, biokinetics and their role in petroleum and mining industries. Biochem Eng J 44: 73-94.

Telang AJ, Ebert S, Foght JM, Westlake DWS, Voordouw G. (1998). Effects of two diamine biocides on the microbial community from an oil field. Can J Microbiol 44: 1060-1065.

Trueper HG, Schlegel HG. (1964). Sulphur metabolism in thiorhodaceae. I. quantitative measurements on growing cells of chromatium okenii. Antonie Van Leeuwenhoek 30: 225-238.

Vance I, Thrasher DR (2005). Reservoir souring: Mechanisms and prevention. Petroleum Microbiology. American Society of Microbiology. Washington, DC pp. 123-142.

Voordouw G, Grigoryan AA, Lambo A, Lin S, Park HS, Jack TR et al. (2009). Sulfide remediation by pulsed injection of nitrate into a low temperature Canadian heavy oil reservoir. Environ Sci Technol 43: 9512-9518.

Whitham TS, Gilbert PD. (1993). Evaluation of a model biofilm for the ranking of biocide performance against sulphate-reducing bacteria. J Appl Bacteriol 75: 529-535.

Widdel F, Kohring G-W, Mayer F. (1983). Studies on dissimilatory sulfate-reducing bacteria that decompose fatty acids. Archives of Microbiology 134: 286-294.

Fida, T.T. et al., "Synergy of Sodium Nitroprusside and Nitrate in Inhibiting the Activity of Sulfate Reducing Bacteria in Oil-Containing Bioreactors", Frontiers in Microbiology, May 16, 2018, vol. 9, article 981, pp. 1-11. Retrieved from: https://www.ncbi.nlm.nih.gov/pmc/articles/PMC5965020/pdf/fmicb-09-00981.pdf.

Xue Y. et al., "Control of Microbial Sulfide Production with Biocides and Nitrate in Oil Reservoir Simulating Bioreactors", Frontiers in Microbiology, Dec. 8, 2015, vol. 6, article 1387, pp. 1-11. Retrieved from: https://www.ncbi nlm nih gov/pmc/articles/PMC4672050/.

Mand, J., "Microbial Ecology of Carbon Steel Corrosion", University of Calgary thesis, Jan. 2017. Retrieved from: https://prism.ucalgary.ca/handle/11023/3588.

Batai, I et al., "The Growth of Bacteria in Intravenous Glyceryl Trinitrate and in Sodium Nitroprusside", Anesthesia and Analgesia, Dec. 1999 vol. 89, No. 6, pp. 1570-1572. Retrieved from: https://journals.1ww.com/anesthesia-analgesia/fulltext/1999/12000/The Growth of Bacteria in Intravenous Glycery1.49.aspx.

International Search Report and Written Opinion issued in corresponding International Application No. PCT/CA2018/051097 dated Nov. 7, 2018.

Kryachko, et al. Microbially enhanced oil recovery from miniature model columns through stimulation of indigenous microflora with nitrate; International Biodeterioration & Biodegradation 96 (2014) 135e143.

\* cited by examiner

SODIUM NITROPRUSSIDE AND NITRATE METABOLIC INHIBITION OF SULFATE-REDUCING MICROBES TO CONTROL SULFIDE PRODUCTION

FIELD

The invention is in the field of microbiology, particularly the use of inorganic compounds to regulate bacterial growth and activity.

BACKGROUND

Formation of hydrogen sulfide ($H_2S$), a process commonly referred to as souring, results from the growth and activity of sulfate-reducing bacteria (SRB) and sulfate reducing archaea (SRA), collectively referred to as sulfate-reducing microorganisms (SRM). SRM anaerobically respire sulfate to sulfide as part of their energy metabolism. Souring is a common problem in the petroleum industry, in reservoirs and in surface processing facilities of oil production operations, under low- and high-temperature as well as saline or fresh water conditions. Depending on the pH, sulfide may be present as $H_2S$ in all three phases or as $HS^-$ and as $S^{2-}$ in the aqueous phase (Gieg et al., 2011). Souring must generally be controlled due to the increased risk to health and safety, deterioration of oil and gas quality, and biocorrosion of pipelines and steel infrastructure (Hubert et al., 2005; Tang et al., 2009; Vance and Thrasher, 2005). Souring is commonly controlled by the application of biocide or nitrate (Bødtker et al., 2008; Xue and Voordouw, 2015). Biocides, such as benzalkonium chloride (BAC), glutaraldehyde (Glut), bronopol, formaldehyde, cocodiamine (Coco), and tetrakishydroxymethyl phosphonium sulfate (THPS) are organic chemicals commonly applied to injection waters and production facilities to kill SRM and other microorganisms (Vance and Thrasher, 2005; Xue and Voordouw, 2015). Nitrate application enriches nitrate-reducing bacteria (NRB), which inhibit SRB by outcompeting for electron donors, increasing the redox potential, or producing nitrite which is an inhibitor of dissimilatory sulfite reductase (Dsr) responsible for reduction of sulfite to sulfide (Bødtker et al., 2008; Voordouw et al., 2009; Xue and Voordouw, 2015).

The application of biocides has several drawbacks including environmental concerns from non-target toxicity, and economics of application (Fraise, 2002; Telang et al., 1998; Whitham and Gilbert, 1993). Other problems are the need for high concentrations (slugs) and frequent (e.g. weekly) treatments, especially when dealing with biofilms (Kjellerup et al., 2005; Vance and Thrasher, 2005). Some biocides react with sulfide in reservoirs in a manner, which compromises their efficacy. Therefore, the choice of biocide and the optimal dosing strategy are important in the oil industry to maximize efficient control of souring.

Sodium nitroprusside (SNP; $Na_2[Fe(CN)_5NO].2H_2O$) has been widely used as a vasodilating drug for treatment of pulmonary hypertension (Koslyk et al., 2015; Lim and Zaphiriou, 2016). A bactericidal effect of SNP has been reported for *Pseudomonas aeruginosa*, *Clostridium sporogenes*, and *Bacillus subtilis* (Barraud et al., 2006; Joannou et al., 1998; Moore et al., 2004). In studies of its physiological importance as a vasodilating drug, SNP has been reported to react with $H_2S$ biosynthesized in mammals during enzymatic metabolism of sulfhydryl proteins (Quiroga et al., 2011).

In the context of the present application, various terms are used in accordance with what is understood to be the ordinary meaning of those terms. For example, "petroleum" is a naturally occurring mixture consisting predominantly of hydrocarbons in the gaseous, liquid or solid phase. In the context of the present application, the words "petroleum" and "hydrocarbon" are used to refer to mixtures of widely varying composition. The production of petroleum from a reservoir necessarily involves the production of hydrocarbons, but is not limited to hydrocarbon production. Similarly, processes that produce hydrocarbons from a well will generally also produce components of petroleum fluids that are not hydrocarbons. In accordance with this usage, a process for producing petroleum or hydrocarbons is not necessarily a process that produces exclusively petroleum or hydrocarbons, respectively. "Fluids", such as petroleum fluids, include both liquids and gases. Natural gas is the portion of petroleum that exists either in the gaseous phase or is in solution in crude oil in natural underground reservoirs, and which is gaseous at atmospheric conditions of pressure and temperature. Natural gas may include amounts of non-hydrocarbons.

It is a common practice to segregate petroleum substances of high viscosity and density into categories, such as "light oil", "heavy oil" and "bitumen". For example, some sources define "heavy oil" as a petroleum that has a mass density of greater than about 900 $kg/m^3$. Bitumen is sometimes described as that portion of petroleum that exists in the semi-solid or solid phase in natural deposits, with a mass density greater than about 1,000 $kg/m^3$ and a viscosity greater than 10,000 centipoise or 10 Pa·s measured at original temperature in the deposit and atmospheric pressure, on a gas-free basis. Although these terms are in common use, references to heavy oil and bitumen represent categories of convenience, and there is a continuum of properties between heavy oil and bitumen. Accordingly, references to heavy oil and/or bitumen herein include the continuum of such substances, and do not imply the existence of some fixed and universally recognized boundary between the two substances. In particular, the term "heavy oil" includes within its scope all "bitumen" including hydrocarbons that are present in semi-solid or solid form.

A reservoir is a subsurface (or subterranean) formation containing one or more natural accumulations (or deposits) of moveable petroleum, which are generally confined by relatively impermeable rock. An "oil sand" (or formerly "tar sand") reservoir is generally comprised of strata of sand or sandstone containing petroleum. A reservoir represents one type of hydrocarbon-containing environment or system, which may support microbial growth or metabolism. Alternative hydrocarbon-containing environments or systems may include oil field production or other petroleum handling facilities. In these environments and systems, it is desirable to provide compositions and methods that may be used so as to ameliorate souring.

SUMMARY

Combinations of a nitroprusside, such as sodium nitroprusside (SNP; $Na_2[Fe(CN)_5NO].2H_2O$) and a nitrate, may be used as metabolic inhibitors of microbial cultures, for example cultures that include sulfate reducing bacteria (SRB). As exemplified in aqueous SRB culture, this metabolic inhibition may for example be implemented in the presence of a hydrocarbon, for example in an oil reservoir or in oil field systems and facilities. When applied to an SRB culture in the presence of a hydrocarbon, the combination of SNP and a nitrate may accordingly be used to ameliorate the biological formation of sulfides, particularly hydrogen sulfide.

DETAILED DESCRIPTION

Compositions are provided that comprise a combination of a nitroprusside salt or a solvate thereof, such as SNP, with a nitrate salt or a solvate thereof, such as sodium nitrate. In select embodiments, synergistic combinations, for example of SNP and nitrate, may be provided, for example in aqueous solution, where the amounts of the nitroprusside and nitrate are synergistically effective to inhibit microbial metabolism. Methods are accordingly provided for the combined use of a nitroprusside salt or a solvate thereof, such as SNP, with a nitrate salt or a solvate thereof, such as sodium nitrate. In use, nitroprussides and nitrates may be combined in amounts that are effective to inhibit microbial metabolism, for example in microbial cultures that include sulfate reducing bacteria (SRB). As exemplified in aqueous SRB culture, this metabolic inhibition may for example be implemented in the presence of a hydrocarbon, for example in an oil reservoir or in connate or produced water environments. When applied to an SRB culture, the combination of SNP and a nitrate may accordingly be used to ameliorate the biological formation of sulfides, such as hydrogen sulfide. In the context of a hydrocarbon-containing environments or systems, such as an oil or gas reservoir or oil field production facilities, this may for example be implemented so as to ameliorate souring.

Nitroprusside salts available for use in accordance with alternative aspects of the present innovations may for example be an alkali salt, such as sodium nitroprusside or potassium nitroprusside, or a mixture or hydrate thereof, such as disodium nitroprusside dihydrate.

Nitrate salts available for use in accordance with alternative aspects of the present innovations may for example be alkali salts, such as sodium nitrate or potassium nitrate, or calcium nitrate, or mixtures thereof.

In select embodiments, SNP may be used in concentrations from 1-50 ppm in combination with 85 ppm nitrate, or from 26-131 ppm in the absence of nitrate, to inhibit the metabolism or growth of microbes, such as SRBs. This may for example be carried out in oil field systems (i.e. reservoirs and surface facilities). In select embodiments, this may for example be carried out so as to decrease, ameliorate or eliminate sulfides in sour systems.

In select embodiments, as exemplified herein, pulsing of 1 ppm SNP while continuously injecting 85 ppm of nitrate gave control of souring in oil bioreactors. Individually, souring control was achieved by using 50 ppm of SNP or 340 ppm of nitrate. These numbers indicate that SNP and nitrate, when applied together, are highly synergistic in inhibiting souring.

In the presence of sulfide, SNP may be used to inhibit steel corrosion, for example at concentrations of 0.5-1 mM (150-300 ppm). This inhibition of corrosion may for example be carried out with SNP applied so as to also control the metabolism or growth of microbes, such as SRB.

In an exemplified embodiment, growth and activity of SRB was completely inhibited by SNP concentrations, as low as 50 µM (14.9 ppm), when applied before the cells started growing in serum bottles ($10^4$ SRB/ml). Similarly, an SNP concentration of 0.5 mM (149 ppm) completely inhibited the growth of SRB consortia, when applied to mid-log phase cultures ($10^7$ SRB/ml).

In select embodiments, SNP may be used so as to react chemically with sulfide, and thereby remove sulfides, for example from aqueous environments, such as a hydrocarbon reservoir or a hydrocarbon processing facility.

In one embodiment, monitoring of most probable numbers (MPNs) indicated application of 0.5 mM (149 ppm) SNP for 1 h to actively growing cells killed SRB $10^9$-fold and acid producing bacteria (APB) $10^7$-fold. The growth and activity of mid-log phase thermophilic SRB consortia at 60° C. in the presence of 0.5 M NaCl was prevented by SNP concentrations as low as 50 µM (15 ppm). This illustrates that SNP could be used as souring inhibitor in both high temperature reservoirs and in reservoirs flooded with seawater, which may for example contain about 0.5 M NaCl.

Examples

Materials and Methods
Bacterial Culture and Growth Medium

The bacterial culture used in this example was obtained from produced water samples designated 4PW, 14PW or 18PW of the Medicine Hat Glauconitic C (MHGC) oil field near Medicine Hat, Alberta, Canada. Coleville synthetic brine medium A or K [CSBA or CSBK (Callbeck et al., 2013; Hubert et al., 2003)], with an $N_2$ (90% v/v) and $CO_2$ (10%) ($N_2$—$CO_2$) headspace was used for enrichment and growth of SRB consortia. CSBK medium contained (g/L) (NaCl (1.5), $KH_2PO_4$ (0.05), $NH_4Cl$ (0.32), $CaCl_2.2H_2O$ (0.21), $MgCl_2.5H_2O$ (0.54), and KCl (0.1) whereas CSBA medium contained (g/L) (NaCl (30), $KH_2PO_4$ (0.2), $NH_4Cl$ (0.2), $CaCl_2.2H_2O$ (0.15), $MgCl_2.5H_2O$ (0.4), and KCl (0.5). The media were buffered with bicarbonate ($NaHCO_3$, 30 mM). One ml each of trace elements and tungstate/selenite solution (Widdel et al., 1983) were added separately. The pH was adjusted to 7.4 using 2 M HCl. The serum bottles were sealed with butyl rubber septa and tightened with aluminum crimp seals. Sodium sulfate was used as the electron acceptor and volatile fatty acids (VFA: a mixture of acetate, propionate and butyrate), lactate, or MHGC heavy oil (API 16) were used as electron donor for enrichment of SRB at concentrations indicated below.

Souring Control in Bioreactors Containing Heavy Oil

Figure 1:
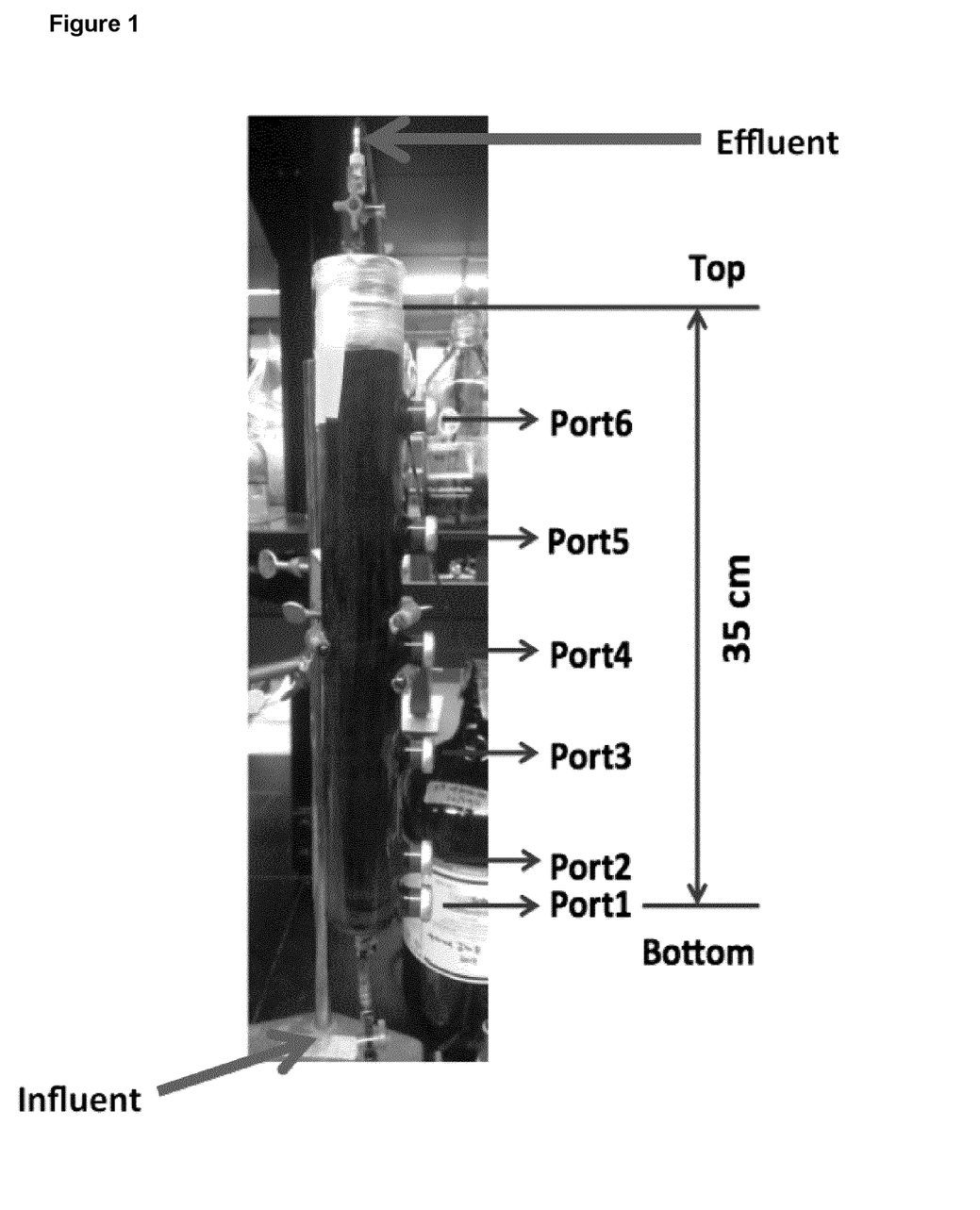
FIG. 1 is an image of sand packed oil column showing the locations of sampling ports and the flow direction (from influent to effluent) within the column.

Glass barrel columns (500 ml) were provided with a layer of glass wool and a layer of polymeric mesh and were then packed tightly with sand (Sigma-Aldrich, 50-70 mesh), followed by a top layer of glass wool (Gassara et al., 2015; Kryachko and Voordouw, 2014). The typical column had 6 sampling ports sealed with rubber stoppers and aluminum rings, allowing sampling at different positions along the flow path (FIG. 1). A larger stopper perforated with a syringe was used to seal the column outlet. Two Luer-Lock three-way valves were connected to the inlet and outlet syringe of the column. The columns were injected with CSBK under upward flow conditions using a Gilson MiniPuls 3 peristaltic pump to make them water wet. The columns were weighed before and after saturation to measure the pore volumes (typically 120 ml). The columns were then flooded with 1 PV of MHGC heavy oil, replacing about 0.95 PV of CSBK. Oil was then produced from the columns by injection of anoxic CSBK medium containing 2 mM sulfate from a 2 L medium reservoir at a rate of 0.5 PV per day until the column contained about 0.5 PV of residual oil. The columns were then injected with 1 PV of SRB consortia from MHGC produced water (18PW) enriched with CSBK containing MHGC oil with additional sulfate (5 mM). The columns were incubated for one month to allow cell proliferation, followed by a continuous flooding of CSBK-S(CSBK with 2 mM sulfate) at a rate of 0.25 PV per day. After establishment of constant souring (effluent sulfide concentrations approaching 2 mM), the medium was amended subsequently with 1 ppm SNP+43 ppm (0.5 mM) nitrate, 1 ppm SNP+85 ppm (1 mM) nitrate or 1 ppm SNP+170 ppm (2 mM) nitrate in duplicate bioreactors. To illustrate the SRB inhibitory effect of SNP and nitrate combination with SNP or nitrate alone, the bioreactors received subsequent concentrations of 10 and 50 ppm of SNP or 85, 170 and 340 ppm (4 mM) of nitrate. The bioreactors were treated with 2 PV at each concentration of SNP, nitrate or combinations. Sulfide and sulfate concentrations were then determined by sampling 300 ul of fluids from the different ports and from the effluent using syringe needles.

Determination of an Exemplary Minimum Inhibitory Concentration of SNP at Low Temperature in Batch Cultures Two conditions were used to illustrate an exemplary minimum inhibitory concentration of SNP on SRB in batch culture in serum bottles. The first condition was the use of SNP on a nondense SRB culture at the start of growth. Different concentrations of SNP dihydrate (1, 10, 25, 50 µM; 10 µM=3 ppm) were added to 20 ml of CSBK medium containing 2 mM $Na_2SO_4$ and 3 mM of each VFA in 60 ml serum bottles closed with butyl rubber stoppers. SNP was added with a syringe attached to a 25-gauge needle from a 50 mM stock solution anaerobically prepared in CSBK medium in the dark. The bottles were then inoculated with 100 µl SRB consortia from 18PW already enriched for 96 h on CSBK medium with 3 mM VFA and 2 mM sulfate. In the second condition, SNP (10, 25, 50, 100, 500, 1000 µM; 1000 µM=298 ppm) was added to mid-log phase cultures of an SRB consortium. The cultures were grown in duplicate in 350 ml CSBK medium with 15 mM of each VFA and 10 mM sulfate in 500 ml bottles closed with butyl rubber stoppers and sealed with open top bottle caps. After reduction of about 5 mM sulfate (i.e. in midlog phase), 20 ml of the cultures together with about 10 ml headspace gas were transferred with a syringe to 60 ml serum bottles closed with butyl rubber stoppers and filled with $N_2$—$CO_2$. The selected concentrations of SNP were then immediately added to each bottle. The experiments were done in duplicate for each concentration and the bottles were incubated at 30° C. in the dark. Samples (0.5 ml) were periodically withdrawn and concentrations of sulfate, sulfide, SNP, nitrate, nitrite and protein were monitored as described below.

Determination of an Exemplary Minimum Inhibitory Concentration of SNP at High Temperature and Salinity in Serum Bottles Similar experiments as for mesophilic SRB were conducted to illustrate the efficacy of SNP at high temperature and sea water salinity. Thermophilic SRB (tSRB) were obtained as an enrichment culture of produced water samples of the Terra Nova oil field. This oil field has a resident temperature of 95° C. and is located offshore from Newfoundland, Canada. The samples were enriched at 60° C. in CSBA medium containing 0.5 M NaCl, 10 mM sulfate and 20 mM lactate. The tSRB were grown in 400 ml CSBA medium with 20 mM lactate and 8 mM sulfate in a 500 ml bottle closed with a butyl rubber stopper and sealed with an open top bottle cap. After 4 mM sulfate was reduced, 20 ml of the culture were transferred with a syringe to 60 ml serum bottles closed with butyl rubber stoppers and filled with $N_2$—$CO_2$. SNP (either 25, 50, 100, 200, 500 or 1000 μM) was added immediately. Samples were incubated at 60° C. and sulfate reduction was monitored over time.

Chemical Reaction of SNP and Sulfide

A blue-colored product was observed immediately after addition of SNP to mid-log phase cultures indicating chemical reaction of SNP and sulfide. Therefore, the concentrations of SNP and sulfide before and after the reaction were determined, as indicated below. SRB were grown in CSBK medium containing 3 mM VFA and 2 mM sulfate at 30° C. After complete reduction of sulfate to sulfide, SNP (2 mM) was added. The concentrations of SNP and sulfide were then determined repeatedly over a 120 min period.

SNP Kill of SRB and Acid Producing Bacteria (APB)

An actively growing anaerobic culture of SRB, which also contained APB, was obtained from a continuous culture in CSBK medium with 4 mM lactate and 2 mM sulfate. Subcultures (10 ml) were transferred with a syringe to duplicate 60 ml serum bottles closed with butyl rubber stoppers and an $N_2$—$CO_2$ headspace. SNP was added to 0.5 mM (149 ppm). Controls without SNP were kept under the same conditions. After 10 min, 1 h and 24 h of exposure to SNP, aliquots (100 μl) of the cultures were serially diluted in triplicate in 48-well microtiter plates containing Postgate medium B (900 μl). Postgate medium B contains (g/L): $KH_2PO_4$ (0.5), $NH_4Cl$ (1.0), $CaSO_4$ (1.0), $MgSO_4.7H_2O$ (2.0), sodium lactate (4.0:60% w/w), yeast extract (1.0), ascorbic acid (0.1), thioglycolate (0.1), $FeSO_4.7H_2O$ (0.5). APB were enumerated by growing triplicates of the serially diluted samples on phenol red broth (Difco, BD). The samples were incubated anaerobically for 3 weeks at 30° C. in the hood. Wells exhibiting a black precipitate for or a yellow color were scored positive for growth of SRB and APB, respectively. Most probable numbers (MPNs) were derived from the data using appropriate statistical tables (Shen and Voordouw, 2015).

Corrosion Inhibition

Four different approaches were used to illustrate the corrosion inhibitory activity of SNP. The first approach was to test the concentration-dependent corrosivity of SNP on carbon steel coupons under abiotic conditions. One pre-cleaned, pre-weighed carbon steel coupon (a366, 2×1×0.1 cm) was added to 20 ml of CSBK medium with 2 mM sulfate and 3 mM VFA in 50 ml serum bottles with a headspace of $N_2$—$CO_2$. Different concentrations of SNP (0, 0.1, 0.5, 1, 1.5 and 2 mM; 1 mM=298 ppm) were then added to each bottle. The second approach was to determine whether SNP enhances or inhibits corrosion in a sour system. SRB consortia were grown in CSBK medium containing 2 mM sulfate and 3 mM VFA, as described above. After complete reduction of sulfate to about 2 mM sulfide, carbon steel coupons and different concentrations of SNP was added as described above. The third approach was to test corrosion rates when SNP was allowed to react with sulfide before it came in contact with steel. SNP (0.5 mM) was added to 20 ml of a sour SRB culture containing approximately 2 mM sulfide. Coupons were then added to this mixture within 1 min, 1 h or 24 h after mixing. The fourth approach was to test whether thiocyanate (SCN-) formed from SNP (Filipovic et al., 2013) decreases corrosion of carbon steel in the presence or absence of sulfide. Potassium thiocyanate (2 mM) was added to CSBK medium in the presence or absence of SNP (2 mM) and in the presence or absence of sulfide (2 mM) and SNP (2 mM). In all approaches, triplicate samples were incubated in the dark at 30° C. on a rocker for one month. Weight loss corrosion rates were measured following this incubation.

Comparison of SNP with Other Compounds

Different concentrations of SNP (5, 10, 20 or 40 ppm) were compared with the same concentrations of the compounds BAC, Glut, BAC_Glut (a combination of BAC and Glut), THPS and cocodiamine (Coco). The experiments were conducted in 19 ml CSBK medium containing 20 mM sulfate and 10 mM lactate in 25 ml Hungate tubes. To each tube, 5 carbon steel beads were added and the medium was inoculated with 1 ml of 4PW SRB consortia, obtained by enrichment from 4PW. After one month of incubation at room temperature, the concentrations of sulfate, sulfide and lactate and the corrosion rates were determined.

Analytical Methods

Samples (0.5 ml) were transferred to a microfuge tube and centrifuged at 17,000×g for 5 min. Concentrations of sulfate, nitrate and nitrite were determined from the clarified fluid with high-performance liquid chromatography (HPLC), using a Waters 1515 HPLC instrument equipped with a Waters 2489 UV/visible detector (for nitrate and nitrite) or a Waters 432 conductivity detector (for sulfate) and an IC-PAK Anion HC, 4.6×150-mm column (Waters, Japan) as described elsewhere (Grigoryan et al., 2008). The SNP concentration was determined, using a Waters 1515 HPLC instrument equipped with a Waters 2489 UV/visible detector and a Nova-PAK C18, 3.9×150-mm column (Waters, Japan). Methanol:water (95:5%) was used as the mobile phase for detection of SNP. Samples (100 μl) were diluted in 400 μl of the mobile phase and injected (50 μl) at a flow rate of 1 ml/min. The peak of SNP was detected at 210 nm and concentrations were estimated from known concentrations of SNP standards prepared in CSBK medium. The aqueous sulfide concentration was determined colorimetrically with N,N-dimethyl-p phenylenediamine reagent (Trueper and Schlegel, 1964).

Protein concentrations were determined as described elsewhere (Fida et al., 2014). Briefly, 0.5 ml of samples were pelleted by centrifugation at 17,000×g for 5 min. The cell pellets were suspended in 100 μl of 0.1 N NaOH, lysed by heating at 95° C. for 10 min and centrifuged for 1 min at 16,000×g to remove cell debris. The protein concentration was quantified with a Qubit fluorimeter (Invitrogen) using the Qubit protein assay Kit (Invitrogen).

Results and Discussion

Souring Control in Oil Bioreactors

Figure 2:
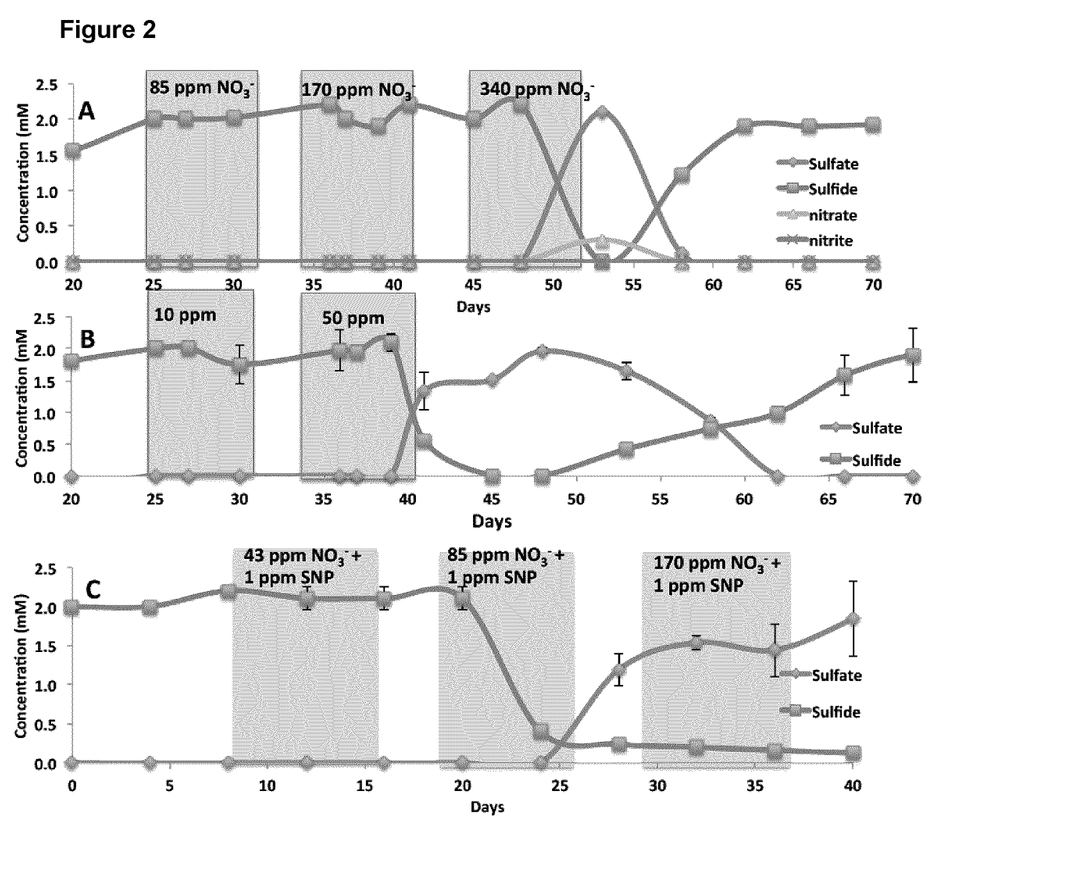
FIG. 2 includes three line graphs, illustrating sulfate and sulfide concentrations at the effluents of the oil-containing bioreactors. Sulfate, sulfide, nitrate and nitrite concentrations in bioreactors treated with nitrate (A); sulfate and sulfide concentrations in bioreactors treated with SNP (B); sulfate and sulfide concentration in bioreactors treated with combinations of SNP and nitrate (C). Shaded regions indicate duration for continuous injection of 2 PV (240 ml).

Sulfide and sulfate concentrations in the effluent and at the different ports were recorded during flooding of oil-containing bioreactors, which contained an active SRB consortium, with CSBK-S. Injection of 2PV (240 ml) of CSBK-S with 85 ppm (1 mM) or 170 ppm (2 mM) of nitrate did not affect the sulfide concentration in the effluent (FIG. 2A). However, inhibition of sulfate reduction was observed with injection of 2 PV (240 ml) of 340 ppm (4 mM) of nitrate (FIG. 2A). Only partial conversion of sulfate to sulfide was observed at port 1, whereas almost complete conversion of sulfate to sulfide was observed at port 2 for all three nitrate concentrations (0, 85 and 170 ppm). The injection of 2 PV (240 ml) of CSBK-S with 50 ppm (0.17 mM) of SNP resulted in souring control, which lasted long after injection of SNP was terminated at 40 days (FIG. 2). Sulfide concentrations decreased to zero at 45 days and sulfate concentrations reached 2 mM at 48 days (FIG. 2B) after which sulfide concentrations in the effluent slowly increased again. In the absence of SNP partial reduction of sulfate to sulfide was observed at port 1. Amendment with 10 ppm of SNP pushed sulfate reduction to port 3 while 50 ppm completely inhibited sulfate reduction at all the ports and in the effluent (FIGS. 3C and 3D).

Figure 3:
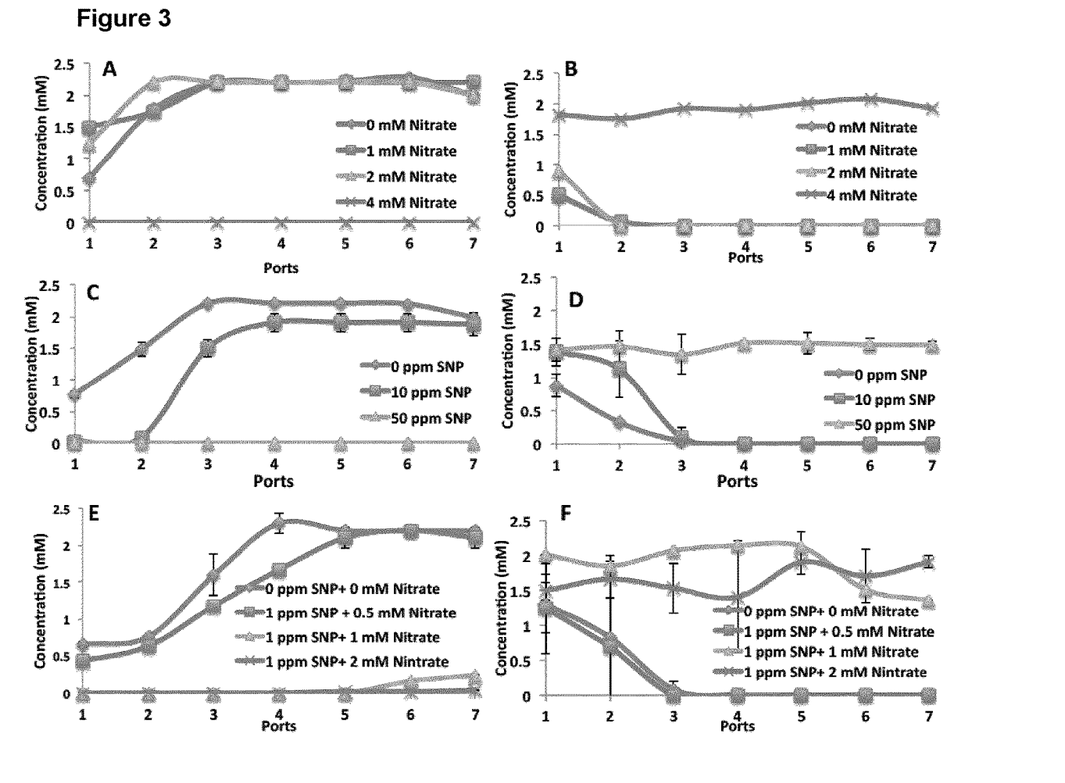
FIG. 3 includes six line graphs, illustrating sulfate and sulfide concentrations at the different ports of the oil-containing bioreactors. Sulfide concentration in bioreactors treated with nitrate (A), sulfate concentration in bioreactors treated with nitrate (B), sulfide concentration in bioreactors treated with SNP (C), sulfate concentration in bioreactors treated with SNP (D), sulfide concentration in bioreactors treated with SNP and nitrate combination (E), sulfate concentration in bioreactors treated with SNP and nitrate combination (F). Port 7 is effluent of the bioreactors.

Hence, when used singly, 340 ppm of nitrate and 50 ppm of SNP inhibited sulfate reduction in bioreactors in which oil was the electron donor. However, combinations of nitrate and SNP proved to be more efficient. A combination of 1 ppm of SNP and 85 ppm (1 mM) of sodium nitrate inhibited souring in effluent of the bioreactors (FIG. 2C), as well as at ports 1 to 6 (FIGS. 3 E and F). Inhibition was also observed with 1 ppm of SNP and 170 ppm (2 mM) of sodium nitrate, but not in this example with 1 ppm of SNP and 43 ppm (0.5 mM) of sodium nitrate. (FIG. 2C, FIGS. 3 E and F). These results exemplify a strong synergistic inhibitory effect on SRB when SNP is used in combination with nitrate. This synergistic effect facilitates the use of minimized doses of SNP and/or nitrate to inhibit SRB, minimizing costs associated with souring control and decreasing potential environmental impacts from using higher doses. The result also indicate that, in the exemplified embodiments, SNP is not reacting in a significant fashion with oil components, so that it maintained an inhibitory activity in the presence of hydrocarbons. Therefore, as low as 1-10 ppm of SNP when combined with 100-200 ppm of nitrate can be used as a metabolic inhibitor of SRB activities in reservoirs where souring is detected.

Effect of SNP on Batch Cultures of Mesophilic SRB

Figure 4:
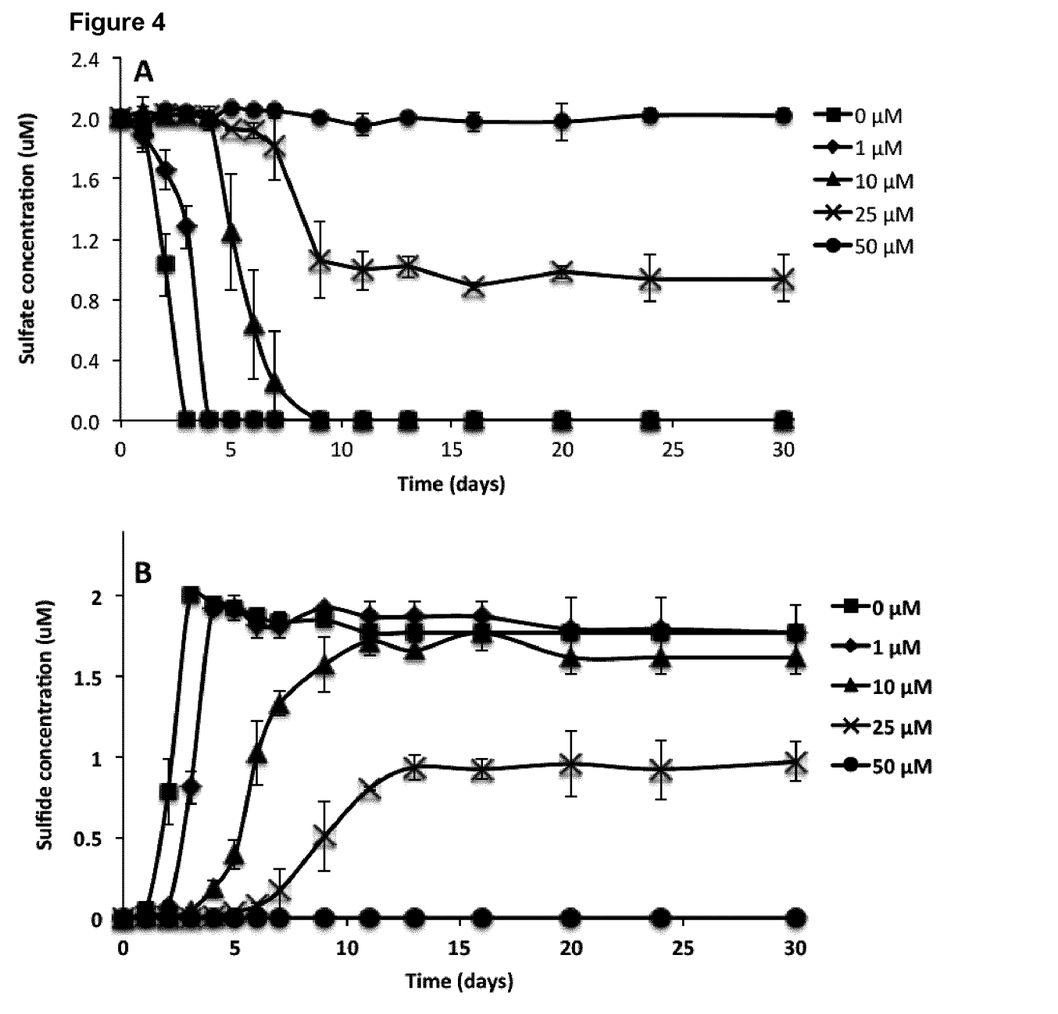
FIG. 4 includes two line graphs, illustrating sulfate reduction (A) and sulfide production (B) by batch cultures of SRB in CSBK medium (2 mM sulfate, 3 mM VFA, 30° C.) in the presence of different concentrations of SNP added at the start of cultivation (t=0 days); 50 µM of SNP is 14.9 ppm.

The minimum concentration of SNP required to inhibit growth of SRB consortia in serum bottles is exemplified at the start and in the middle of the growth curve. When SNP was added to the culture at the start, very low concentrations (less than 25 µM; 7.45 ppm) were required to inhibit the growth of SRB. Sulfate reduction or sulfide accumulation was incomplete at 25 µM and was not observed at and above 50 µM (14.9 ppm) (FIG. 4A, 4B). This indicates that a minimum concentration of SNP may be determined for use in particular circumstances, and in the exemplified embodiment 50 µM of SNP is required to inhibit SRB activity when added to culture medium with little SRB biomass. Compared with other compounds, such as BAC, Glut, BAC-_Glut, THPS and Coco, an SNP dosage of 10 ppm completely inhibited the metabolic activity and growth of SRB as judged by a low sulfide, and high sulfate and lactate concentrations (FIG. 5A-C), whereas other compounds were not effective at this low dosage.

Figure 6:
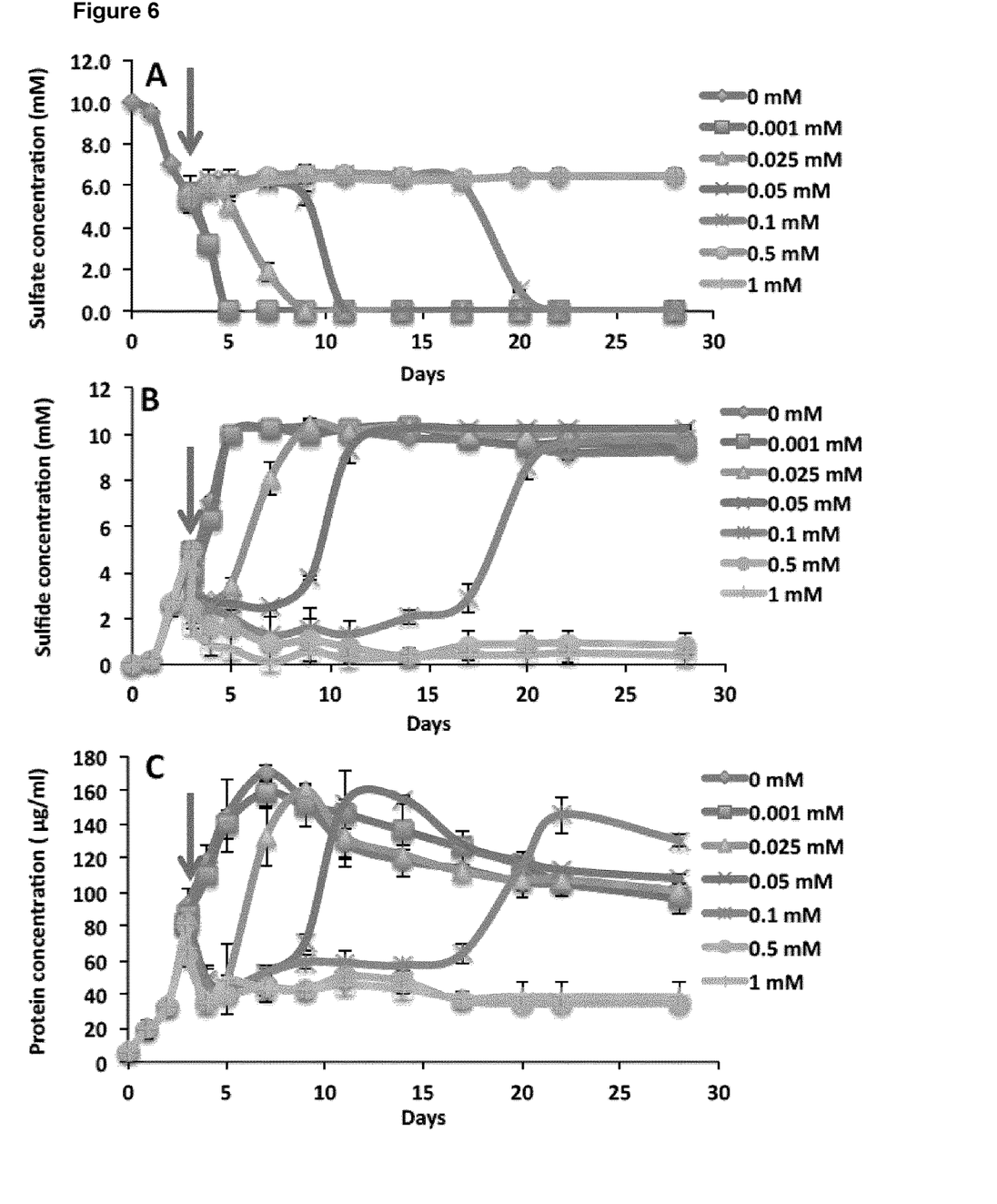
FIG. 6 includes three line graphs, illustrating sulfate reduction (A), sulfide production (B) and protein concentration (C) of cultures of mesophilic SRB grown in CSBK medium (10 mM sulfate, 15 mM VFA, 30° C.) in the presence of different concentrations of SNP added to the culture at the mid log phase of growth (↓); 1 mM SNP is 298 ppm.

When added to batch cultures of SRB in serum bottles at mid-log phase, an SNP concentration of 0.1 mM (29.8 ppm) extended the time needed for complete sulfate reduction from 5 to 20 days (FIGS. 6A and 6B). No sulfate reduction, or accumulation of sulfide was observed at SNP concentrations of 0.5 and 1.0 mM (FIGS. 6A and 6B). No increase in protein concentration was observed at these concentrations, illustrating that SNP inhibits the growth of SRB and other bacteria (FIG. 6C).

Figure 7:
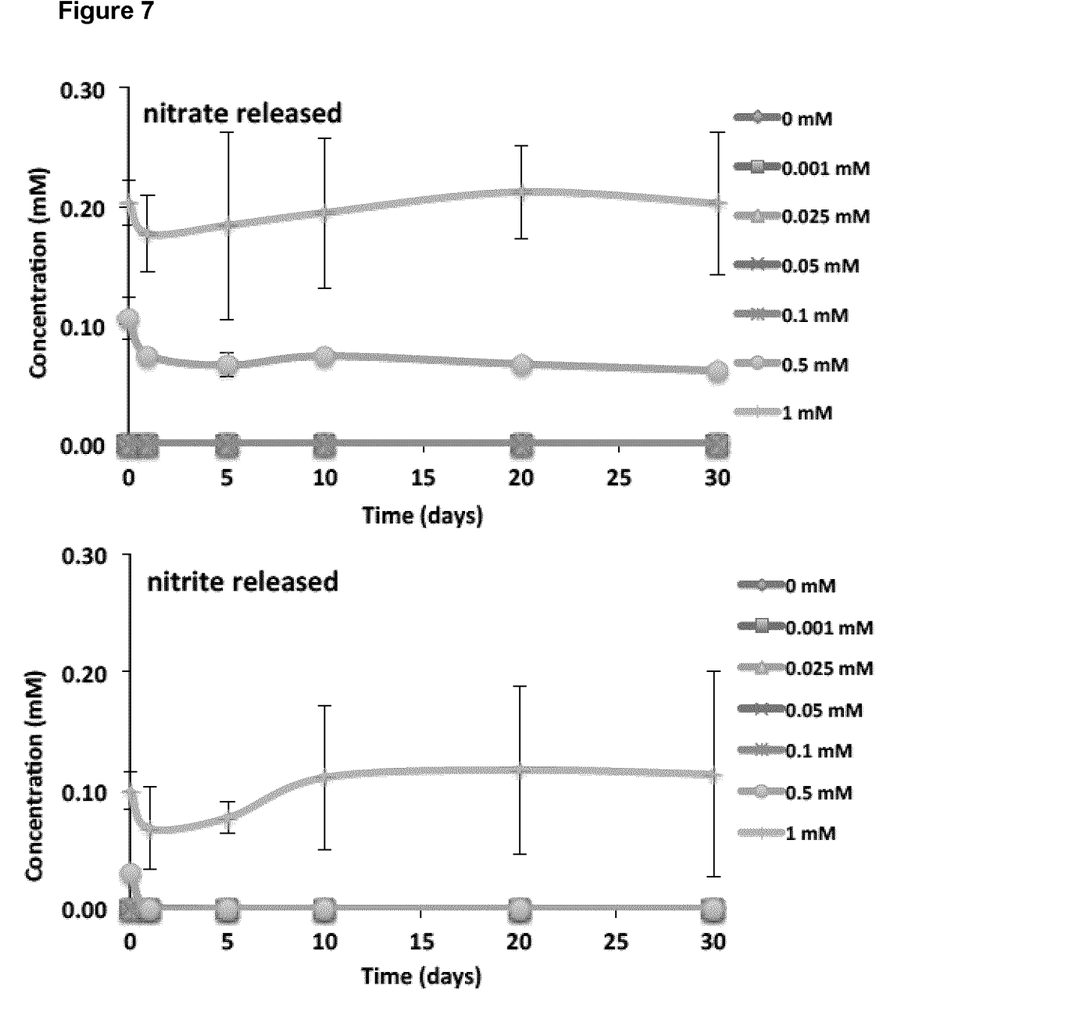
FIG. 7 includes two line graphs, illustrating concentrations of nitrate and nitrite detected in mid-log phase cultures of mesophilic SRB consortia as in FIG. 6 after addition of different concentrations of SNP.

Accumulation of 0.1 and 0.2 mM nitrate was detected in mid-log phase cultures following addition of 0.5 or 1 mM SNP, respectively (FIG. 7), whereas accumulation of 0.1 mM nitrite was detected with 1 mM SNP only. Nitrate or nitrite accumulation was not detected in cultures to which lower concentrations of SNP were added.

Concentration-Dependent Inhibition of Thermophilic SRM

Figure 8:
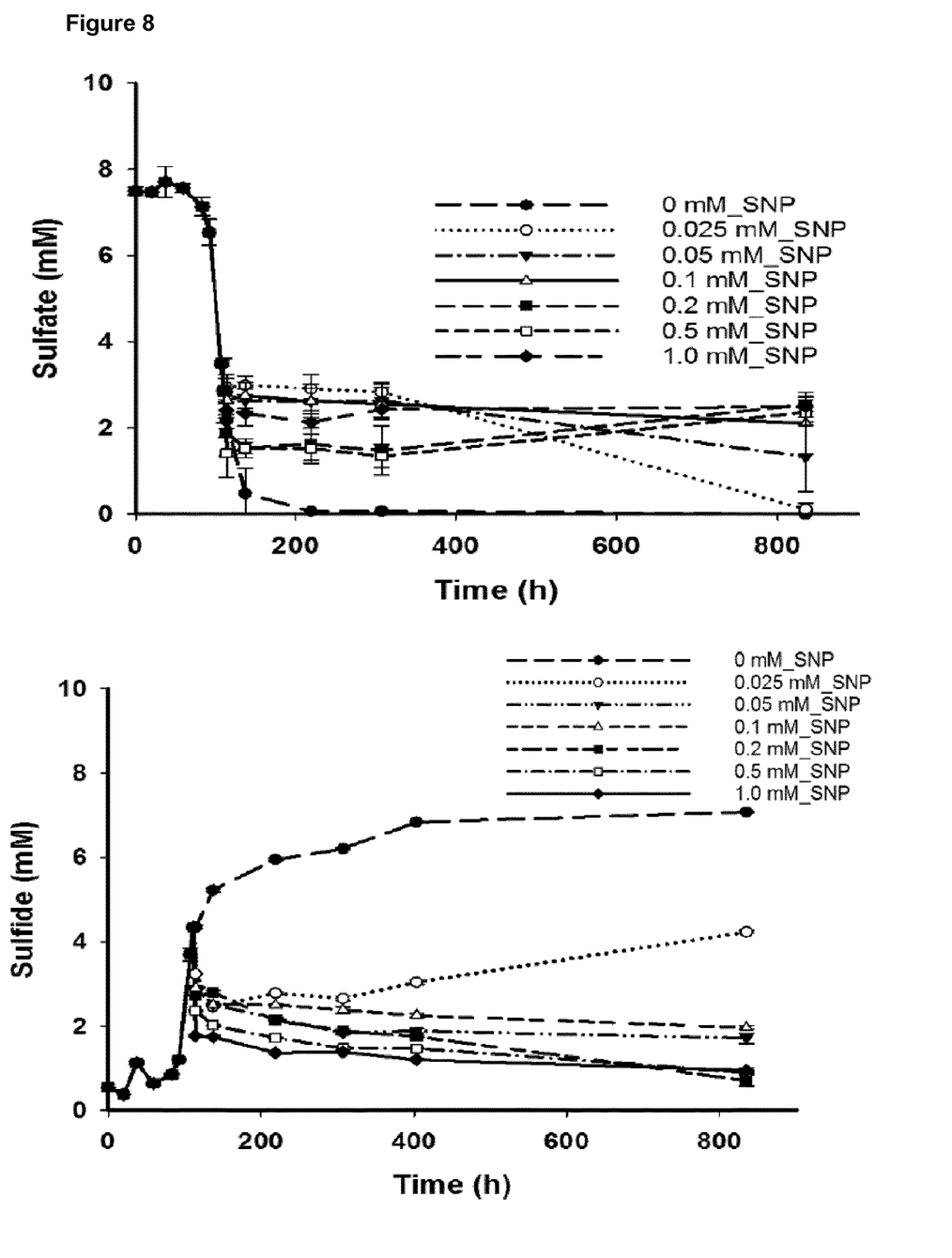
FIG. 8 includes two line graphs, illustrating sulfate reduction (A) and sulfide production (B) in a batch culture of thermophilic SRB grown in CSBA medium (8 mM sulfate, 20 mM lactate, 60° C.) in the presence of different concentrations of SNP added at mid-log growth phase; 1 mM SNP is 298 ppm.

To illustrate the applicability of SNP at high temperature and salinity, concentration dependent inhibition of a culture of thermophilic sulfate-reducing microorganisms (tSRM) was determined at 60° C. in CSBA medium with 0.5 M NaCl. The inhibition of tSRM was observed at lower SNP concentrations than that of mesophilic SRB. Reduction of sulfate to sulfide was not observed at and above 0.05 mM SNP (FIG. 8A, 8B), whereas this was between 0.1 and to 0.5 mM for mSRB. SNP reacted chemically with sulfide at 60° C. as illustrated by the immediate decrease of sulfide concentration upon addition of SNP. This decrease was also observed at low temperature (FIG. 6B), but at higher SNP concentrations. These results illustrate that SNP inhibits and/or kills tSRM and removes sulfide already formed at high temperature conditions. This characteristic may for example be utilized in embodiments such as high temperature oil reservoirs flooded with seawater, which has approximately 0.5 M NaCl. Unlike at low temperature conditions, complete removal of sulfide was not observed at high temperature even in the presence of 1 mM SNP (FIG. 8).

Chemical Reaction of SNP with Sulfide

Figure 9:
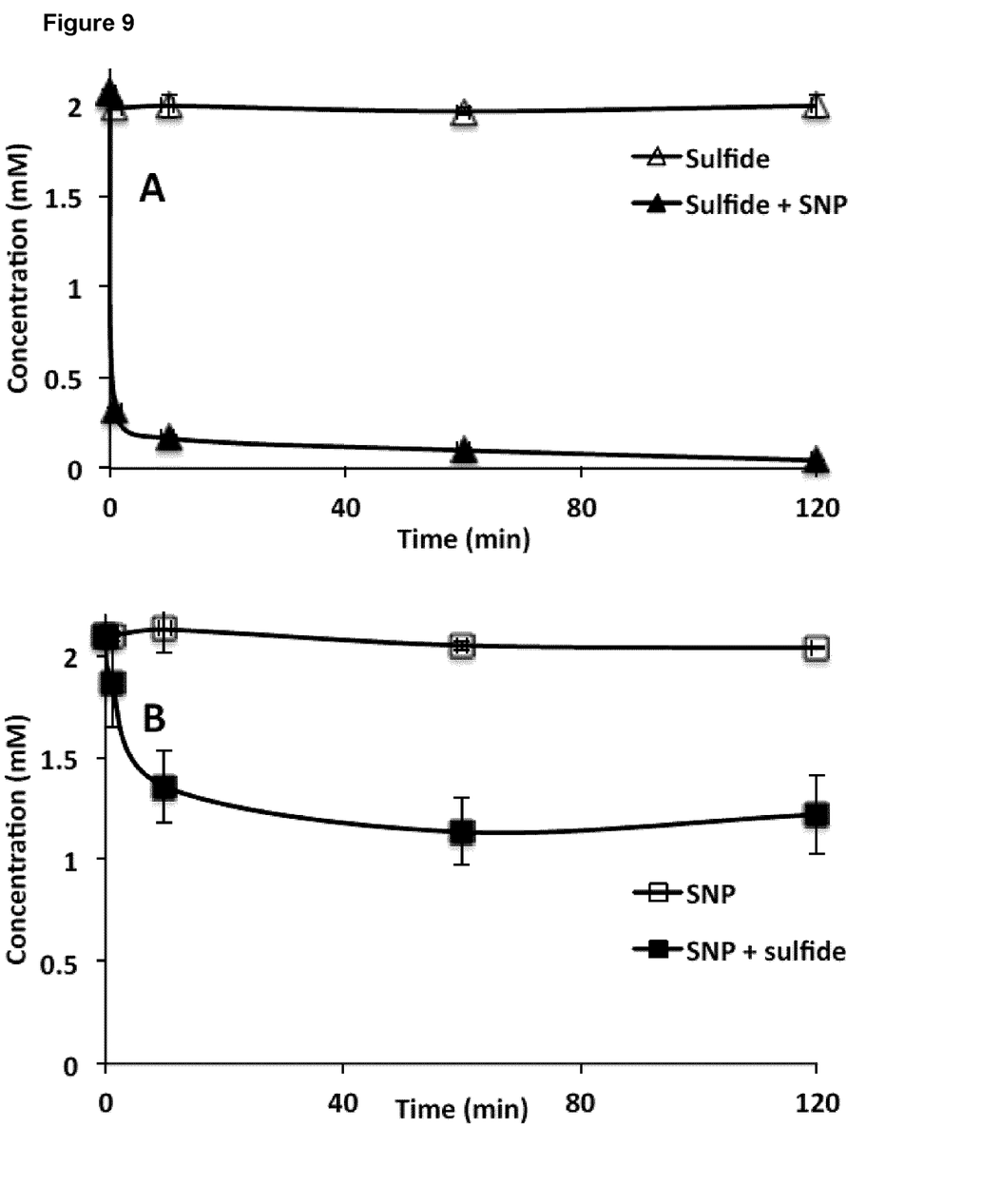
FIG. 9 includes two line graphs, illustrating change in sulfide concentration (A) and SNP concentration (B) after reaction of 2 mM of SNP with 2 mM of sulfide. Controls were 2 mM sulfide without SNP (A) or 2 mM SNP without sulfide (B).

An important finding illustrated by this example is that SNP not only inhibits and kills SRB but, under certain conditions, may also chemically react with the sulfide formed. Addition of SNP to a sour system generated transient formation of multiple reaction products with distinct colors. Upon addition of 0.5 mM SNP to 2 mM sulfide, a Prussian blue type color was immediately formed, which changed to a dark blue color within a minute. In this example, the dark blue color changed to dark green within 1 h and then to a brownish color over 24 h, which remained stable. These changes in color indicated the occurrence of chemical reactions between SNP and sulfide, which is also evident from the disappearance of sulfide and removal of the typical $H_2S$ smell from the bottles. Addition of 2 mM SNP to 2 mM sulfide resulted in disappearance of all sulfide within 2 h and a decrease of SNP concentration from 2 to 1.2 mM (FIGS. 9A and 9B).

Effect of SNP on MPNs of SRB and APB

Figure 10:
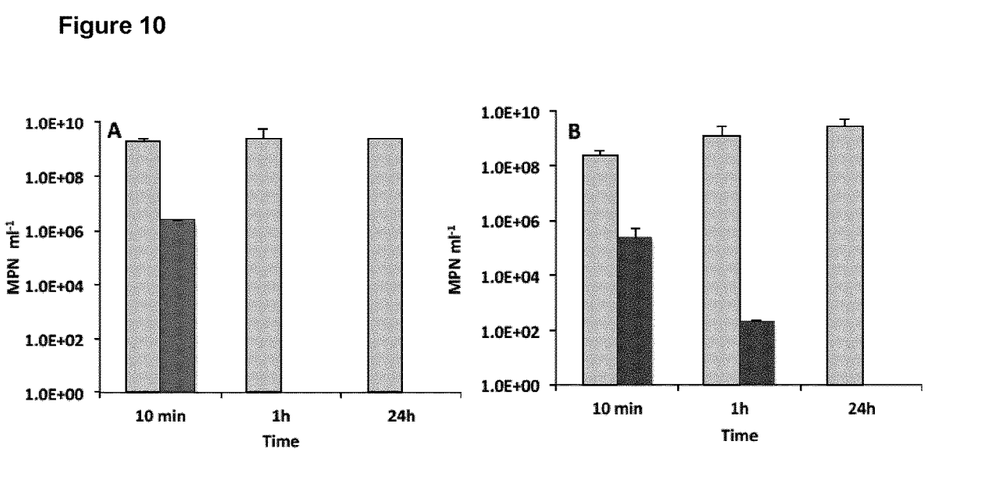
FIG. 10 includes two bar graphs, illustrating MPNs of SRB (A) and APB (B) after 10 min, 1 h and 24 h exposure of actively growing consortia to 0.5 mM SNP (black bars), compared with MPNs for consortia not exposed to SNP (grey bars).

Determination of MPNs illustrates that SNP effectively killed SRB and APB. The killing of SRB was about $10^3$-fold within 10 min and $10^9$-fold or more after 1 h (FIG. 10A). Similarly, APB killing was about $10^3$-fold within 10 min, $10^5$- to $10^6$-fold within 1 h and more than $10^9$-fold after 24 h (FIG. 10B). The result illustrates that SNP kills SRB more effectively than APB.

SNP-Mediated Corrosion

Figure 5:
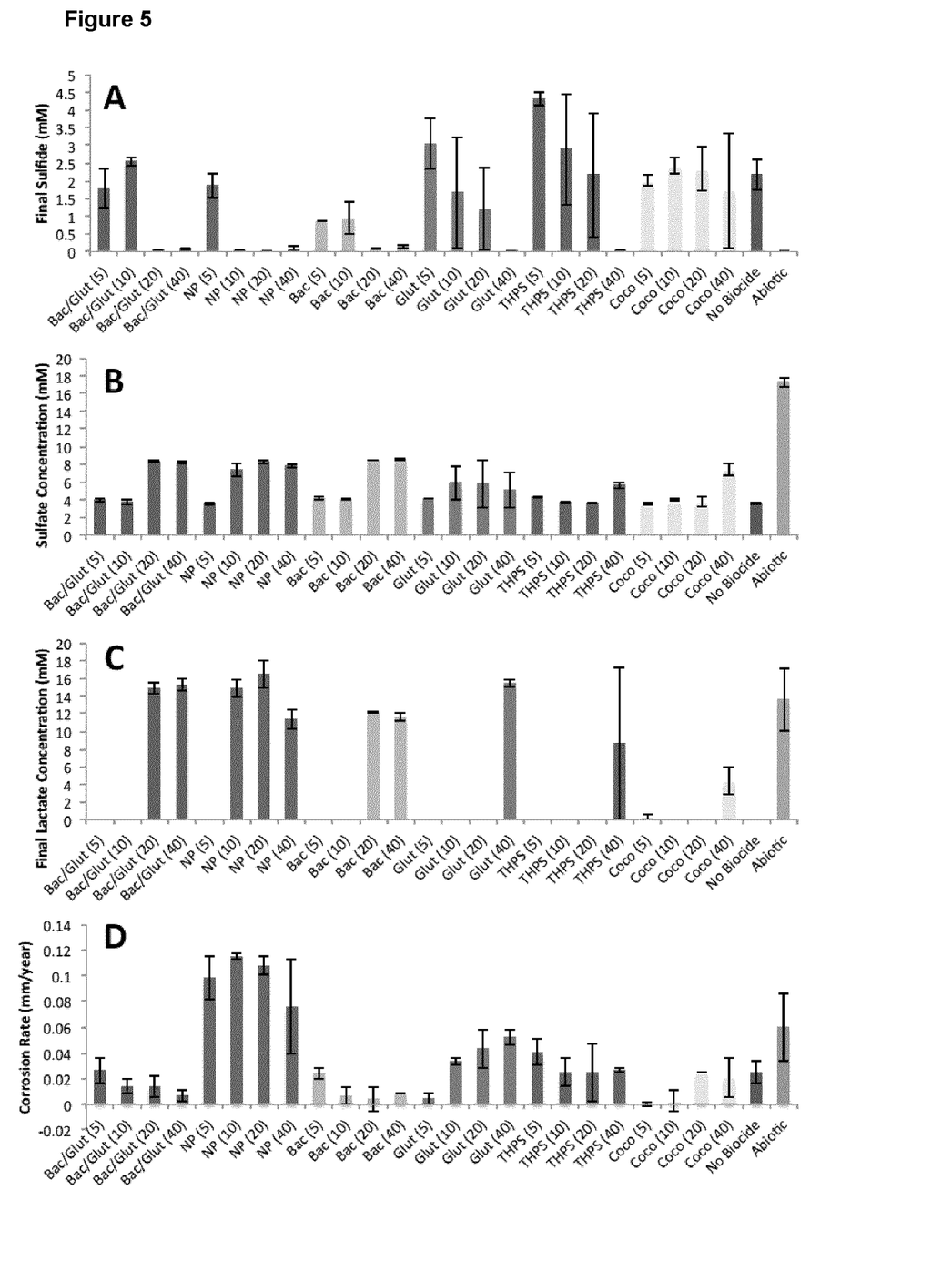
FIG. 5 includes four bar graphs, illustrating comparison of effect of SNP and other biocides at 5, 10, 20 or 40 ppm added at the start of growth on souring and corrosion. Concentrations of (A) sulfide, (B) sulfate and (C) lactate, as well as (D) weight loss corrosion rates of carbon steel beads were determined after one month of incubation at 23° C. with shaking in duplicate.
Figure 11:
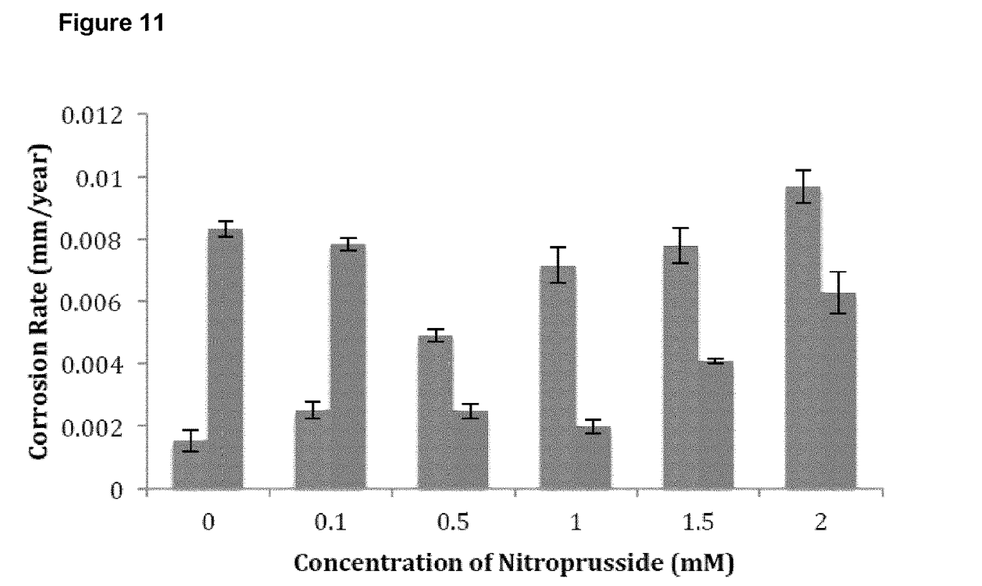
FIG. 11 is a bar graph illustrating general weight loss corrosion rates of carbon steel coupons exposed to 0 to 2 mM SNP in the absence (blue bars) or presence (red bars) of 2 mM sulfide. Each value is the mean of three replicates and SEM is shown.
Figure 12:
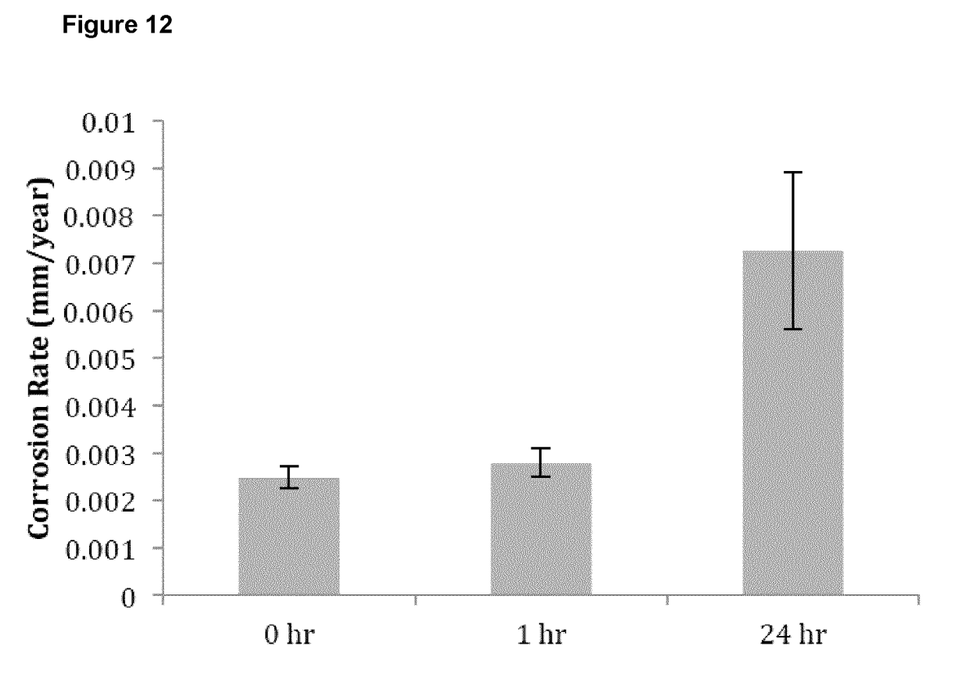
FIG. 12 is a bar graph illustrating general weight loss corrosion rates of carbon steel coupons exposed to products of the reaction of SNP (0.5 mM) and sulfide (2 mM). The coupons were exposed immediately (0 h), 1 h or 24 h after reaction. Mean weight loss corrosion rates of three replicates are shown and error bars indicate standard error of the mean.

The corrosivity of SNP was tested on steel coupons in the presence or absence of sulfide. General corrosion rates of coupons increased from 0.0015 to 0.009 mm/yr with increasing concentrations of SNP in the absence of sulfide (FIG. 11). Relative to other compounds, SNP was more corrosive to carbon steel beads in the absence of sulfide (FIG. 5D). Interestingly, addition of up to 1 mM SNP to a sour medium decreased the corrosion rates of carbon steel coupons from 0.008 to 0.002 mm/yr (FIG. 11). In particular, addition of 0.5 or 1 mM of SNP decreased corrosion to a rate comparable to that of the abiotic control with no sulfide or SNP (0.0018 mm/yr). These results illustrate that SNP may be used so as to decrease corrosion when added to a sour system.

CONCLUSIONS

The foregoing Examples illustrate a strong synergistic effect of SNP and nitrate. Together, these are potent metabolic inhibitors of SRB activity, as exemplified in heavy-oil containing reservoir models. SNP also strongly inhibited SRB activity in batch cultures. In heavy-oil containing columns, SRB activity was completely inhibited by an SNP concentration of 1 ppm when combined with 170 ppm of nitrate. Individually, in the exemplified embodiment, 50 ppm of SNP and 340 ppm of nitrate were capable of complete inhibition of SRB activity in oil bioreactors. The low dose of 1 ppm of SNP, when combined with 170 ppm nitrate, to control souring in the presence of oil illustrates that the efficacy of SNP is sustained in the presence of hydrocarbons, such as oil or components thereof. In batch cultures in which VFA (not oil) were used as electron donor for sulfate reduction, SRB activity was completely inhibited by an SNP concentration of 0.05 mM (14.9 ppm) in serum bottles when applied early in the growth curve, whereas 0.5 mM (149 ppm) was capable of inhibiting mid-log phase cultures (5 mM sulfide). The MPNs of both SRB and APB were below the detection limit ($10^9$-fold decrease) after 24 h of exposure to 0.5 mM (149 ppm) SNP. SNP was also effective in controlling activity of tSRB at 60° C. and 0.5 M NaCl.

SNP is chemically reactive to steel in the absence of sulfide, which may be a factor taken into consideration when applying high concentration slugs to pipelines, for instance. Importantly, SNP inhibited steel corrosion when applied to a sour system at low concentration, which is of great importance in removing sulfide and protecting sulfide-mediated pipeline corrosion in sour reservoirs and oil processing facilities.

As exemplified, SNP concentrations from 0.1 to 0.5 mM (29.8 to 149 ppm) were effective both in inhibiting the growth of SRB and in eliminating sulfide by chemically reacting in sour systems (2 mM sulfide). Accordingly, in one aspect of the present innovation, lower concentrations of SNP may be used to inhibit SRB than the occupational exposure limit, such as 5 ppm. In some applications, SNP may be applied so as to have a relatively short half-life and decay into common C, N, O, and S containing compounds.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification, or cited by the documents cited herein, are incorporated herein by reference as if each individual publication were specifically and individually indicated to be incorporated by reference herein and as though fully set forth herein. The invention includes all embodiments and variations substantially as hereinbefore described and with reference to the examples and drawings.

REFERENCES

Barraud N, Hassett D J, Hwang S-H, Rice S A, Kjelleberg S, Webb J S. (2006). Involvement of nitric oxide in biofilm dispersal of *Pseudomonas aeruginosa*. *Journal of Bacteriology* 188: 7344-7353.

Bødtker G, Thorstenson T, Lillebo B L, Thorbjornsen B E, Ulvoen R H, Sunde E, Torsvik T (2008). The effect of long-term nitrate treatment on SRB activity, corrosion rate and bacterial community composition in offshore water injection systems. *J Ind Microbiol Biotechnol* 35: 1625-1636.

Callbeck C M, Agrawal A, Voordouw G. (2013). Acetate production from oil under sulfate-reducing conditions in bioreactors injected with sulfate and nitrate. *Appl Environ Microbiol* 79: 5059-5068.

Correa L A, Baptista W, Ferreira L A. (2002). Wet $H_2S$ and $CN^-$ corrosion control through on-site polysulfide generation," 6th conf. on Equipment Technology (Salvador Bahia, Brazil: The Brazilian Association of Non-Destructive Testing and Inspection).

Cortese-Krott M M, Fernandez B O, Santos J L, Mergia E, Grman M, Nagy P et al. (2014). Nitrosopersulfide ($SSNO^-$) accounts for sustained NO bioactivity of S-nitrosothiols following reaction with sulfide. *Redox Biol* 2: 234-244.

Fida T T, Palamuru S, Pandey G, Spain J C. (2014). Aerobic biodegradation of 2,4-dinitroanisole by *Nocardioides* sp. strain JS1661. *Appl Environ Microbiol* 80: 7725-7731.

Filipovic M R, Eberhardt M, Prokopovic V, Mijuskovic A, Orescanin-Dusic Z, Reeh Petal. (2013). Beyond $H_2S$ and NO Interplay: Hydrogen Sulfide and Nitroprusside React Directly to Give Nitroxyl (HNO). A New Pharmacological Source of HNO. *Journal of Medicinal Chemistry* 56: 1499-1508.

Fraise A P. (2002). Biocide abuse and antimicrobial resistance—a cause for concern? *J Antimicrob Chemother* 49: 11-12.

Gassara F, Suri N, Stanislav P, Voordouw G. (2015). Microbially enhanced oil recovery by sequential injection of light hydrocarbon and nitrate in low- and high-pressure bioreactors. *Environ Sci Technol* 49: 12594-12601.

Gieg L M, Jack T R, Foght J M. (2011). Biological souring and mitigation in oil reservoirs. *Appl Microbiol Biotechnol* 92: 263-282.

Grigoryan A A, Cornish S L, Buziak B, Lin S, Cavallaro A, Arensdorf J J et al. (2008). Competitive oxidation of volatile fatty acids by sulfate- and nitrate-reducing bacteria from an oil field in Argentina. *Appl Environ Microbiol* 74: 4324-4335.

Hubert C, Nemati M, Jenneman G, Voordouw G. (2003). Containment of biogenic sulfide production in continuous up-flow packed-bed bioreactors with nitrate or nitrite. *Biotechnol Prog* 19: 338-345.

Hubert C, Nemati M, Jenneman G, Voordouw G. (2005). Corrosion risk associated with microbial souring control using nitrate or nitrite. *Appl Microbiol Biotechnol* 68: 272-282.

Joannou C L, Cui X-Y, Rogers N, Vielotte N, Torres Martinez C L, Vugman N V et al. (1998). Characterization of the bactericidal effects of sodium nitroprusside and other pentacyanonitrosyl complexes on the food spoilage bacterium *Clostridium sporogenes*. *Applied and Environmental Microbiology* 64: 3195-3201.

Kjellerup B V, Veeh R H, Sumithraratne P, Thomsen T R, Buckingham-Meyer K, Frolund B et al. (2005). Monitoring of microbial souring in chemically treated, produced-water biofilm systems using molecular techniques. *J Ind Microbiol Biotechnol* 32: 163-170.

Koslyk J L, Ducci R D, Novak E M, Zetola V F, Lange M C. (2015). Sodium nitroprusside: low price and safe drug to control BP during thrombolysis in AIS. *Arq Neuropsiquiatr* 73: 755-758.

Kryachko Y, Voordouw G. (2014). Microbially enhanced oil recovery from miniature model columns through stimulation of indigenous microflora with nitrate. *Int Biodeterior Biodegr* 96: 135-143.

Lim H S, Zaphiriou A. (2016). Sodium nitroprusside in patients with mixed pulmonary hypertension and left heart disease: Hemodynamic predictors of response and prognostic implications. *Journal of Cardiac Failure* 22: 117-124.

Moore C M, Nakano M M, Wang T, Ye R W, Helmann J D. (2004). Response of *Bacillus subtilis* to nitric oxide and the nitrosating agent sodium nitroprusside. *J Bacteriol* 186: 4655-4664.

Quiroga S L, Almaraz A E, Amorebieta V T, Perissinotti L L, Olabe J A. (2011). Addition and redox reactivity of hydrogen sulfides ($H_2S$/HS(-)) with nitroprusside: new chemistry of nitrososulfide ligands. *Chemistry* 17: 4145-4156.

Rock P A, Swinehart J H. (1966). The kinetics of the aqueous hydrogen sulfide-nitroprusside system. *Inorganic Chemistry* 5: 1078-1079.

Shen Y, Voordouw G (2015). Primers for dsr genes and Most Probable Number method for detection of sulfate-reducing bacteria in oil reservoirs. In, Hydrocarbon and Lipid Microbiology Protocols, McGenity, T., Timmis, K. and B. Nogales (eds), Springer-Verlag, Berlin Heidelberg. DOI 10.1007/8623_2015_72. pp 1-9.

Tang K, Baskaran V, Nemati M. (2009). Bacteria of the sulphur cycle: An overview of microbiology, biokinetics and their role in petroleum and mining industries. *Biochem Eng J* 44: 73-94.

Telang A J, Ebert S, Foght J M, Westlake D W S, Voordouw G. (1998). Effects of two diamine biocides on the microbial community from an oil field. *Can J Microbiol* 44: 1060-1065.

Trueper H G, Schlegel H G. (1964). Sulphur metabolism in thiorhodaceae. I. quantitative measurements on growing cells of chromatium okenii. *Antonie Van Leeuwenhoek* 30: 225-238.

Vance I, Thrasher D R (2005). Reservoir souring: Mechanisms and prevention. *Petroleum Microbiology*. American Society of Microbiology.

Voordouw G, Grigoryan A A, Lambo A, Lin S, Park H S, Jack T R et al. (2009). Sulfide remediation by pulsed injection of nitrate into a low temperature Canadian heavy oil reservoir. *Environ Sci Technol* 43: 9512-9518.

Whitham T S, Gilbert P D. (1993). Evaluation of a model biofilm for the ranking of biocide performance against sulphate-reducing bacteria. *J Appl Bacteriol* 75: 529-535.

Widdel F, Kohring G-W, Mayer F. (1983). Studies on dissimilatory sulfate-reducing bacteria that decompose fatty acids. *Archives of Microbiology* 134: 286-294.

Xue Y, Voordouw G. (2015). Control of microbial sulfide production with biocides and nitrate in oil reservoir simulating bioreactors. *Front Microbiol* 6: 1387.

The invention claimed is:

1. A method of inhibiting the metabolism of a microbial culture, comprising applying an effective amount of a combination of a nitroprusside and a nitrate to the microbial culture.

2. The method of claim 1, wherein the nitroprusside is an alkali metal nitroprusside or a solvate thereof.

3. The method of claim 1, wherein the nitroprusside is sodium nitroprusside (SNP) or a solvate thereof.

4. The method of claim 1, wherein the nitrate is an alkali metal nitrate or solvate thereof.

5. The method of claim 1, wherein the nitrate is sodium or potassium nitrate or solvate thereof.

6. The method of claim 1, wherein the nitroprusside and the nitrate are used in a synergistic combination, that synergistically inhibits the metabolism of the microbial culture.

7. The method of claim 1, wherein the microbial culture comprises a sulfate reducing microorganism (SRM), forming a SRM culture, and the SRM culture comprises one or more of a *Desulfobacterales, Desulfovibrionales, Syntrophobacterales, Desulfotomaculum, Desulfosporomusa, Desulfosporosinus, Thermodesulfovibrio, Thermodesulfobacteria, Thermodesulfobium, Archaeoglobus, Thermocladium* or *Caldivirga* species or other species of Bacteria or Archaea, and wherein the production of sulfides by the SRM culture is inhibited by the nitroprusside and nitrate.

8. The method of claim 1, wherein the microbial culture is an aqueous microbial culture.

9. The method of claim 8, wherein the aqueous microbial culture is saline and comprises at least 0.1, 0.2, 0.3, 0.4 or 0.5 M NaCl.

10. The method of claim 1, wherein the microbial culture comprises a hydrocarbon.

11. The method of claim 10, wherein the microbial culture is in a hydrocarbon-containing system comprising a reservoir and/or a petroleum handling facility.

12. The method of claim 10, wherein the production of sulfides from the metabolism of the hydrocarbon by the microbial culture is inhibited, or synergistically inhibited, by the nitroprusside and the nitrate.

13. A method of inhibiting the metabolism of a microbial culture, wherein the microbial culture comprises a hydrocarbon, comprising applying an effective amount of a nitroprusside to the microbial culture.

14. The method of claim 13, wherein the nitroprusside is an alkali metal nitroprusside or a solvate thereof.

15. The method of claim 13, wherein the nitroprusside is sodium nitroprusside (SNP) or a solvate thereof.

16. A method of inhibiting metal corrosion in a hydrocarbon-containing system comprising a sulfide and a microbial culture, wherein the microbial culture comprises a metabolisable hydrocarbon, and wherein the method comprises applying an effective amount of a nitroprusside to the microbial culture.

17. The method of claim 16, wherein the nitroprusside is an alkali metal nitroprusside or a solvate thereof.

18. The method of claim 16, wherein the nitroprusside is applied in combination with a nitrate.

19. The method of claim 18, wherein the nitrate is an alkali metal nitrate or solvate thereof.

20. The method of claim 18, wherein the nitroprusside and the nitrate are used in a synergistic combination, that synergistically inhibits the metabolism of the microbial culture.

* * * * *